United States Patent [19]

Altenburger et al.

[11] Patent Number: 5,753,667
[45] Date of Patent: May 19, 1998

[54] 1-OXO-2- (PHENYLSULPHONYLAMINO) PENTYLPIPERIDINE DERIVATIVES, THEIR PREPARATION AND THEIR THERAPEUTIC APPLICATION

[75] Inventors: Jean Michel Altenburger, Meudon; Gilbert Lassalle, Clamart, both of France

[73] Assignee: Synthelabo, Le Plessis Robinson, France

[21] Appl. No.: 741,290

[22] Filed: Oct. 30, 1996

Related U.S. Application Data

[62] Division of Ser. No. 577,935, Dec. 22, 1995.

[30] Foreign Application Priority Data

Dec. 23, 1994 [FR] France ................ 94.15549

[51] Int. Cl.[6] ............ A61K 31/44; A61K 31/35; C07D 239/00; C07D 211/84; C07D 307/02; C07D 277/20; C07D 317/00; C07D 333/22
[52] U.S. Cl. ............ 514/269; 514/351; 514/357; 514/459; 514/461; 514/667; 544/242; 546/300; 546/302; 546/335; 546/334; 546/290; 548/187; 548/202; 549/476; 549/491; 549/495; 549/62; 549/65; 549/74; 549/75; 549/76; 564/305
[58] Field of Search ............... 514/269, 351, 514/357, 459, 461, 667, 326, 472, 471, 473; 546/210, 300, 302, 334, 335; 549/33, 46, 63, 475, 484, 476, 491, 495, 62, 65, 74–76; 544/242; 548/187, 202; 564/305

[56] References Cited

U.S. PATENT DOCUMENTS

| | | | |
|---|---|---|---|
| 5,136,043 | 8/1992 | Meier | 548/221 |
| 5,312,828 | 5/1994 | Finkelstein et al. | 514/381 |
| 5,359,132 | 10/1994 | Silber et al. | 562/125 |
| 5,453,430 | 9/1995 | Lassalle et al. | 514/312 |
| 5,484,780 | 1/1996 | Boyd et al. | 514/94 |
| 5,545,630 | 8/1996 | Maienfisch et al. | 514/63 |
| 5,556,981 | 9/1996 | Boyd et al. | 548/503 |
| 5,559,277 | 9/1996 | Beller et al. | 585/469 |
| 5,569,786 | 10/1996 | Pettit et al. | 568/646 |
| 5,602,149 | 2/1997 | Altenburger et al. | 514/326 |

FOREIGN PATENT DOCUMENTS

| | | |
|---|---|---|
| 0 565 396 | 10/1993 | European Pat. Off. |
| WO94/17817 | 8/1994 | WIPO |

*Primary Examiner*—Mukund J. Shah
*Assistant Examiner*—Sabiha N. Qazi
*Attorney, Agent, or Firm*—Jacobson, Price, Holman & Stern, PLLC

[57] ABSTRACT

The present invention provides a compound of formula (I)

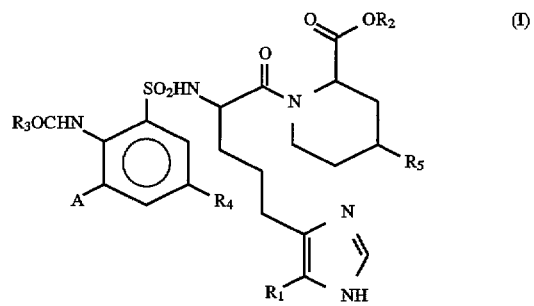

in which $R_1$ represents a hydrogen atom or a ($C_1$–$C_4$)alkyl group, $R_2$ represents a hydrogen atom or a straight or branched ($C_1$–$C_4$)alkyl group, $R_3$ represents a straight or branched ($C_1$–$C_7$)alkyl group, a group —$(CH_2)_nOCH_3$ (where n is 1, 2 or 3) or a group —$CH_2O(C_2H_4O)_mCH_3$ (where m is 1, 2 or 3), $R_4$ represents a hydrogen atom or a halogen atom, $R_5$ represents a straight or branched ($C_1$–$C_4$) alkyl group and A represents phenyl or heterocyclic group optionally substituted with one or more substituents independently chosen from halogen atoms and straight or branched ($C_1$–$C_4$)alkyl, straight or branched ($C_1$–$C_4$)alkoxy and trifluoromethyl groups, or a cyclo($C_5$–$C_8$) alkyl group, in the form of the free base or of a pharmaceutically acceptable addition salt thereof, a process for their preparation and their use in the treatment of thrombosis and thrombotic complications.

1 Claim, No Drawings

1-OXO-2-(PHENYLSULPHONYLAMINO) PENTYLPIPERIDINE DERIVATIVES, THEIR PREPARATION AND THEIR THERAPEUTIC APPLICATION

This is a division of application Ser. No. 08/577,935, filed Dec. 22, 1995.

The present invention relates to 1-oxo-2-(phenylsulphonylamino)pentylpiperidine derivatives, to their preparation and to their therapeutic application.

The present invention provides a compound formula (I)

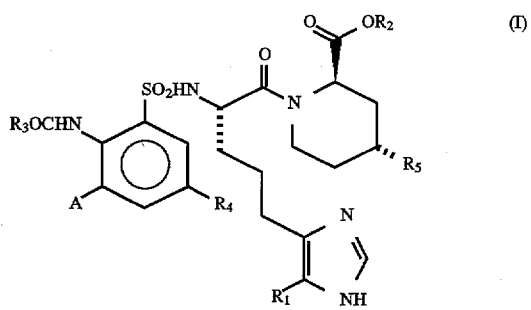

in which $R_1$ represents a hydrogen atom or a $(C_1-C_4)$alkyl group, $R_2$ represents a hydrogen atom or a straight or branched $(C_1-C_4)$alkyl group, $R_3$ represents a straight or branched $(C_1-C_7)$alkyl group, a group $-(CH_2)_nOCH_3$ (where n is 1, 2 or 3) or a group $-CH_2O(C_2H_4O)_mCH_3$ (where m is 1, 2 or 3), $R_4$ represents a hydrogen atom or a halogen atom, $R_5$ represents a straight or branched $(C_1-C_4)$alkyl group and A represents either a phenyl or heterocyclic group optionally substituted with one or more substituents independently chosen from halogen atoms and a straight or branched $(C_1-C_4)$alkyl, straight or branched $(C_1-C_4)$alkoxy and trifluoromethyl groups, or a cyclo$(C_5-C_8)$alkyl group, in the form of the free base or of a pharmaceutically acceptable addition salt thereof.

Preferred compounds according to the invention are those in which:

$R_3$ represents a straight or branched $(C_1-C_7)$alkyl group, and

A represents a pyridyl, thienyl or furyl group, optionally substituted with one or more substituents independently chosen from halogen atoms and straight or branched $(C_1-C_4)$alkyl, straight or branched $(C_1-C_4)$alkoxy and trifluoromethyl groups.

The compounds of the invention possess 3 asymmetric centres. The preferred configuration of the piperidyl group is [2R,4R].

The preferred configuration of the central amino acid part

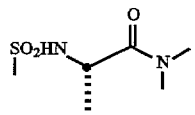

is [S].

The compounds may exist in the form of free bases or addition salts with pharmaceutically acceptable acids.

All of these forms form part of the invention.

In the schemes which follow, the —$CPh_3$ group represents the triphenylmethyl group.

According to the invention, the compounds of formula (I) may in general be synthesized according to Scheme 1.

A sulphonic acid of formula (II), in which A and $R_4$ are as defined above, is reacted with an acid chloride of formula (III) in which $R_3$ is as defined above, generally in an aprotic solvent such as dichloromethane in the presence of a base such as pyridine, followed by addition of triethylamine, generally in excess, to obtain a triethylamine salt of formula (IV); the compound of formula (IV) is then reacted with trifluoroacetic anhydride to obtain a compound of formula (V), from which a compound of formula (VI) is prepared by the action of phosphorus pentachloride generally in a solvent such as dichloromethane; finally, the compound of formula (VI) is reacted with a compound of formula (VII), in which $R_1$ represents a hydrogen atom or a $(C_1-C_4)$alkyl group, $R_2$ represents a straight or branched $(C_1-C_4)$alkyl group and $R_5$ represents a straight or branched $(C_1-C_4)$alkyl group, generally in an aprotic solvent such as dichloromethane in the presence of a base such as triethylamine, then the imidazolyl ring is deprotected and the trifluoroacetyl residue is removed in an acidic medium such as acetic acid/ethanol or acetic acid/tetrahydrofuran/water mixture at reflux, to obtain a compound of formula (I) in which $R_2$ represents a straight or branched $(C_1-C_4)$alkyl group.

Scheme 1

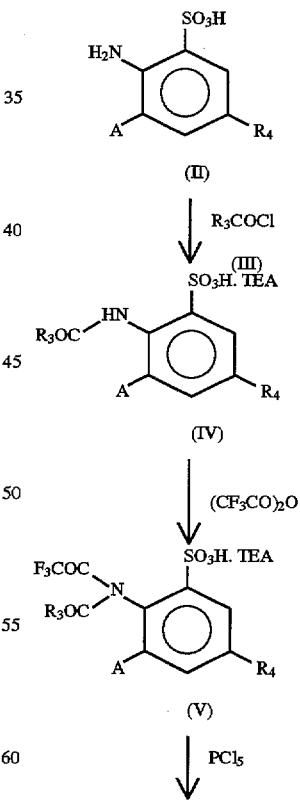

-continued
Scheme 1

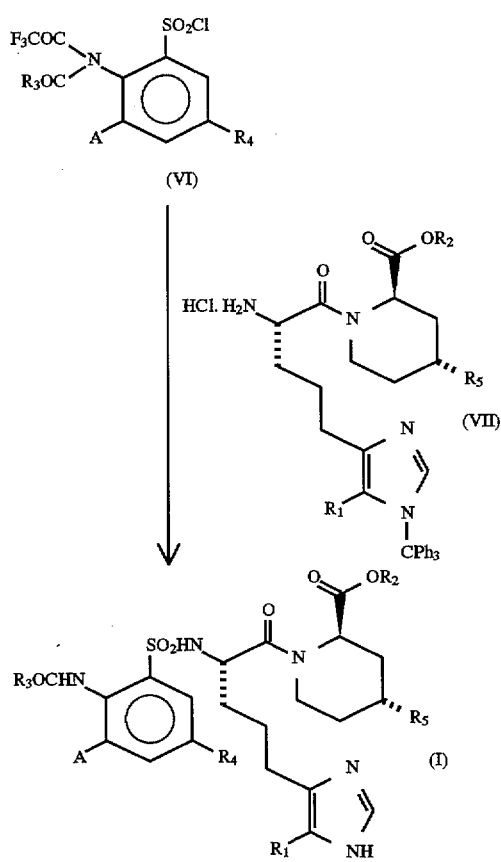

If a compound of formula (I) in which $R_2$ represents a hydrogen atom is desired, the corresponding compound of formula (I) in which $R_2$ represents a straight or branched $(C_1-C_4)$alkyl group is saponified under standard conditions known to those skilled in the art.

In a variant of the process, illustrated in general in Scheme 2, to prepare the compounds of formula (Ia), in which $R'_3$ represents a straight or branched $(C_1-C_7)$alkyl group, a compound of formula (II), which is generally first reacted with triethylamine to form a triethylamine salt, is reacted with an acid chloride of formula (IIIa) or with an anhydride of formula (IIIb), to obtain a symmetrical imide, either in the form of the triethylamine salt of formula (Va) or in the form of the corresponding amine in which case the triethylamine salt of formula (Va) is then prepared, which salt is treated with phosphorus pentachloride to obtain a compound of formula (VIa) which is reacted with a compound of formula (VII) generally in an aprotic solvent such as dichloromethane in the presence of a base such as triethylamine, then the imidazolyl ring is deprotected and one of the residues —$COR'_3$ is removed in an acidic medium such as acetic acid/ethanol, acetic acid/water or acetic acid/tetrahydrofuran/water mixture at reflux, to obtain a compound of formula (Ia) in which $R_2$ represents a straight or branched $(C_1-C_4)$alkyl group.

Scheme 2

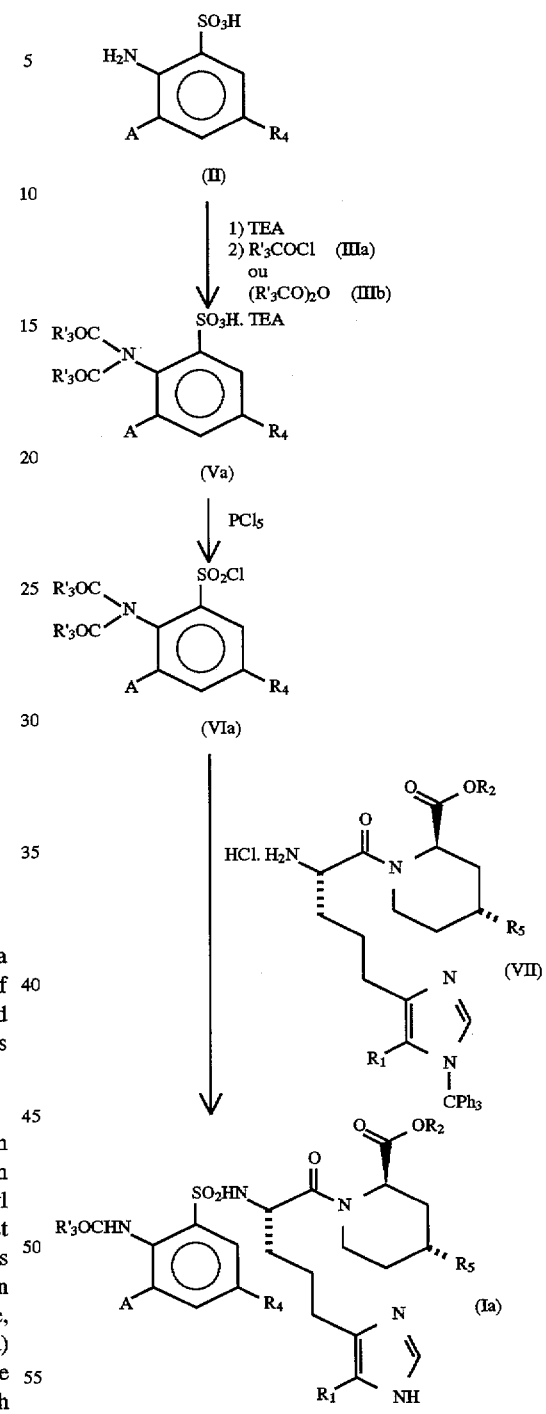

If a compound of formula (Ia) in which $R_2$ represents a hydrogen atom is desired, the corresponding compound of formula (Ia) in which $R_2$ represents a straight or branched $(C_1-C_4)$alkyl group is saponified under standard conditions known to those skilled in the art.

It is also possible to use the process illustrated in general by Scheme 3.

A compound of formula (IIb) in which $R_4$ represents a halogen atom is treated with triethylamine, and the salt thus obtained is reacted with an acid chloride of formula (IIIa), in which R'$_3$ is as defined above, to obtain a compound of formula (IVb), from which a compound of formula (VIb) is prepared by the action of phosphorus pentachloride generally in a solvent such as dichloromethane, followed by reaction of the compound (VIb) with a compound of formula (VII) in which R$_1$ represents a hydrogen atom or a (C$_1$–C$_4$) alkyl group, R$_2$ represents a straight or branched (C$_1$–C$_4$) alkyl group and R$_5$ represents a hydrogen atom or a straight or branched (C$_1$–C$_4$)alkyl group, generally in an aprotic solvent such as dichloromethane, then a residue —COR'$_3$ is removed by treatment in a basic medium such as ammonia in an aprotic solvent, to obtain a compound of formula (VIII), which is reacted with a compound of formula (IX) in which A is as defined above and R is a (C$_1$–C$_4$)alkyl group generally in a solvent such as dimethylformamide in the presence of a

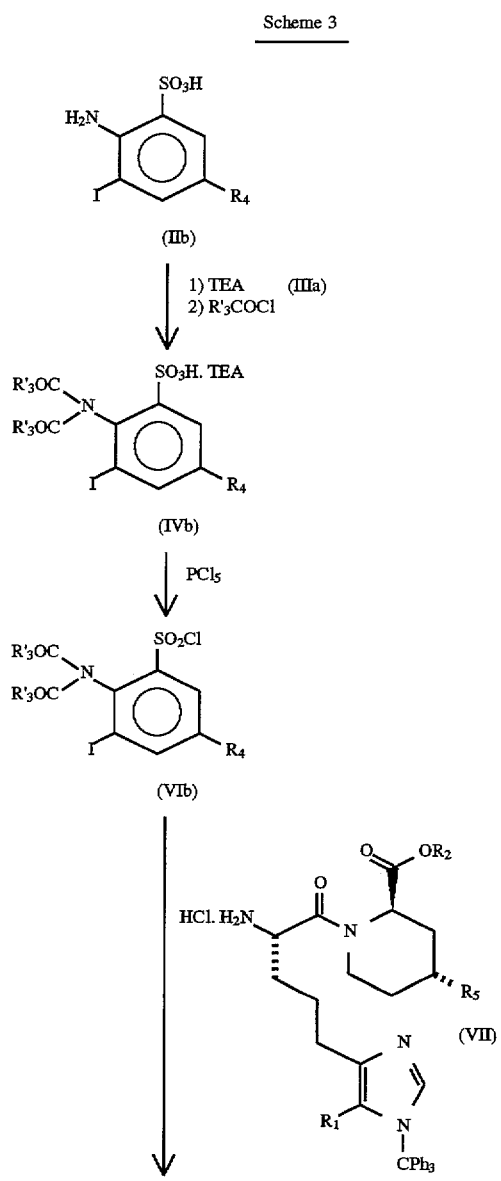

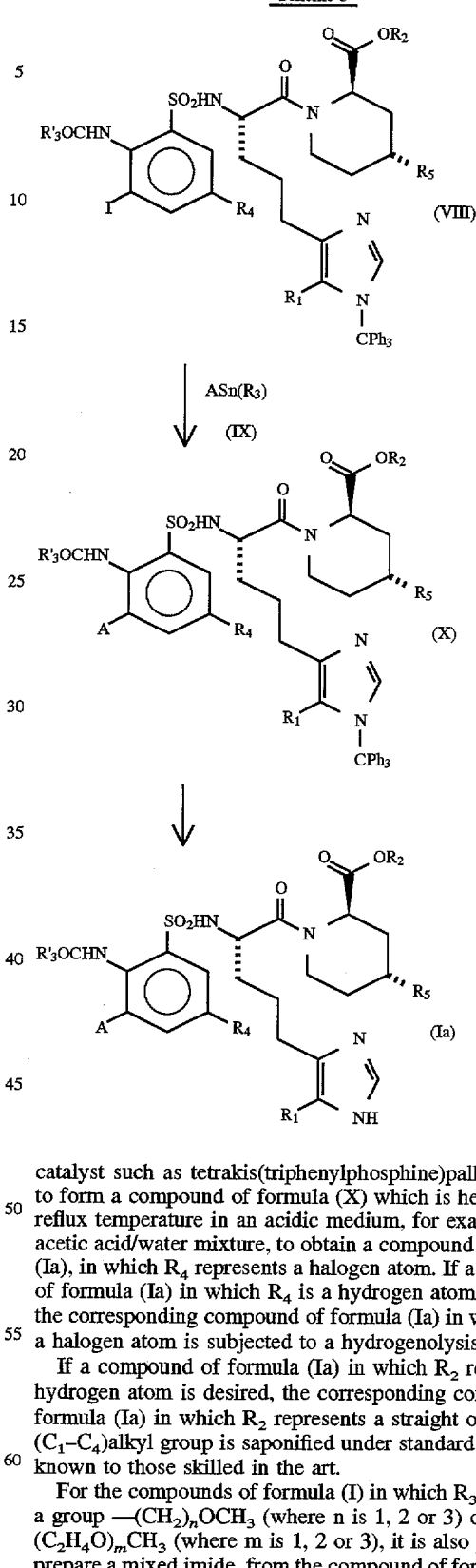

catalyst such as tetrakis(triphenylphosphine)palladium (0), to form a compound of formula (X) which is heated to the reflux temperature in an acidic medium, for example in an acetic acid/water mixture, to obtain a compound of formula (Ia), in which R$_4$ represents a halogen atom. If a compound of formula (Ia) in which R$_4$ is a hydrogen atom is desired, the corresponding compound of formula (Ia) in which R$_4$ is a halogen atom is subjected to a hydrogenolysis.

If a compound of formula (Ia) in which R$_2$ represents a hydrogen atom is desired, the corresponding compound of formula (Ia) in which R$_2$ represents a straight or branched (C$_1$–C$_4$)alkyl group is saponified under standard conditions known to those skilled in the art.

For the compounds of formula (I) in which R$_3$ represents a group —(CH$_2$)$_n$OCH$_3$ (where n is 1, 2 or 3) or —CH$_2$O(C$_2$H$_4$O)$_m$CH$_3$ (where m is 1, 2 or 3), it is also possible to prepare a mixed imide, from the compound of formula (IIb), by a method analogous to that described for the compound of formula (V) in Scheme 1, then the process of Scheme 3 is followed by reacting this mixed imide with the amine of formula (VII).

The compounds of formula (I) or (Ia) obtained in the above processes are optionally converted into addition salts thereof by known methods.

The present invention also provides an intermediate compound of formula (XI)

in which either $R_8$ represents a hydrogen atom or a trifluoroacetyl group, $R_9$ represents a group —$COR_3$ (where $R_3$ is as defined above) and $R_7$ represents a hydroxyl group, or $R_8$ represents a trifluoroacetyl group, $R_9$ represents a group —$COR_3$ and $R_7$ represents a chlorine atom, or $R_8$ and $R_9$ each represents a group —$COR'_3$ (where $R'_3$ is as defined above) and $R_7$ represents a chlorine atom or a hydroxyl group, Z represents an iodine atom, a phenyl or heterocyclic group optionally substituted with one or more substituents independently chosen from halogen atoms and straight or branched ($C_1$–$C_4$)alkyl, straight or branched ($C_1$–$C_4$)alkoxy and trifluoromethyl groups, or a cyclo($C_5$–$C_8$)alkyl group, and $R_4$ is as defined above.

The heterocyclic group is preferably a pyridyl, thienyl or furyl group optionally substitued with one or more substituents chosen from halogen atoms and straight or branched ($C_1$–$C_4$)alkyl, straight or branched ($C_1$–$C_4$)alkoxy and trifluoromethyl groups.

The starting materials are commercially available or are described in the literature or may be prepared according to methods which are described therein or which are known to those skilled in the art.

The compounds of formula (II) and their preparation are described in French patent application No. FR 94/14129. The compounds of formula (VII) are described in European patent application No. EP 0,643,047.

The examples which follow illustrate the preparation of certain compounds in accordance with the invention.

The microanalyses and the IR and NMR spectra confirm the structure of the compounds obtained.

The compound numbers in the examples refer to those in the table given later which illustrates the chemical structures and the physical properties of a few compounds according to the invention.

EXAMPLE 1 (COMPOUND NO. 8)

ethyl [2R-[1(S), 2α, 4β]]-4-ethyl-1-[5-(1H-imidazol-4-yl)-2-[[[2-[(3-methoxy-1-oxopropyl)amino][1,1'-biphenyl]-3-yl]sulphonyl]amino]-1-oxopentyl]piperidine-2-carboxylate hydrochloride 1.1. N,N-diethylethanamine salt of 2-[(3-methoxy-1-oxopropyl)amino][1,1'-biphenyl]-3-sulphonic acid To a solution of 1.74 g (7 mmol) of 2-amino[1,1'-biphenyl]-3-sulphonic acid and 1.6 ml (19.5 mmol) of pyridine in 7 ml of dichloromethane is added dropwise, at 0° C. under a nitrogen atmosphere, a solution of 1.3 g (10.5 mmol) of 3-methoxypropionyl chloride in 3 ml of dichloromethane. The reaction medium is left stirring for 2 hours at 0° C., excess methanol and triethylamine are added and the mixture is then concentrated under reduced pressure. The residue is purified by chromatography on a column of silica gel, eluting with a methanol/dichloromethane/triethylamine mixture (2/98/0.001).

2.3 g of product are obtained in the form of a viscous oil which is used without further purification in the following step.

Yield=100%

1.2. N,N-diethylethanamine salt of 2-[(3-methoxy-1-oxopropyl)(trifluoroacetyl)amino][1,1'-biphenyl]-3-sulphonic acid A mixture of 2.3 g (7 mmol) of the N,N-diethylethanamine salt of 2-[(3-methoxy-1-oxopropyl)amino][1,1'-biphenyl]-3-sulphonic acid and 9.8 ml (70 mmol) of trifluoroacetic anhydride is heated for 3 hours at the reflux temperature, and the reaction medium is then concentrated under reduced pressure.

3.8 g of product are obtained in the form of a viscous oil which is used without further purification in the following step.

Yield=100%

1.3. 2-[(3-methoxy-1-oxopropyl)(trifluoroacetyl)amino][1,1'-biphenyl]-3-sulphonyl chloride To a solution of 3.8 g (7 mmol) of the N,N-diethylethanamine salt of 2-[(3-methoxy-1-oxopropyl)(trifluoroacetyl)amino][1,1'-biphenyl]-3-sulphonic acid in 14 ml of dichloromethane are added 1.75 g (8.4 mmol) of phosphorus pentachloride, the mixture is heated for 3 hours at the reflux temperature and is then concentrated under reduced pressure. The residue thus obtained is purified by chromatography on a column of silica gel, eluting with dichloromethane.

1.3 g of product are obtained in the form of a viscous oil which is used without further purification in the following step.

Yield=40%

NMR (CDCl$_3$), 200 Mhz, δ, (ppm): 8.4–8.2 (m, 1H); 7.8–7.6 (m, 2H); 7.5–7.3 (m, 3H); 7.3–7.2 (m, 2H); 3.8–3.5 (m, 2H); 3.3 (s, 3H); 3.0–2.7 (m, 2H)

1.4. Ethyl [2R-[1(S), 2α, 4β]]-4-ethyl-1-[5-(1H-imidazol-4-yl)-2-[[[2-[(3-methoxy-1-oxopropyl)amino][1,1'-biphenyl]-3-yl]sulfonyl]amino]-1-oxopentyl]piperidine-2-carboxylate hydrochloride To a mixture of 1.5 g (2.4 mmol) of ethyl [2R-[1(S), 2α, 4β]]-1-[-2-amino-1-oxo-5-[1-(triphenylmethyl)-1H-imidazol-4-yl]pentyl]-4-ethylpiperidine-2-carboxylate hydrochloride and 0.8 ml (5.8 mmol) of triethylamine in 15 ml of dichloromethane are added dropwise, at 0° C. under a nitrogen atmosphere, 1.3 g (2.89 mmol) of 2-[(3-methoxy-2-propanoyl)(trifluoroacetyl)]amino[1,1'-biphenyl]-3-sulphonyl chloride dissolved in 3 ml of dichloromethane. The reaction medium is left stirring at this temperature for 6 hours and is then concentrated under reduced pressure. The residue is taken up in 50 ml of ethyl acetate and is then washed successively with 50 ml of aqueous 0.5N hydrochloric acid solution, then with 50 ml of 5% sodium hydrogen carbonate solution and then with 50 ml of saturated sodium chloride solution, and is dried over magnesium sulphate. The residue thus obtained is heated at 90° C. for 2 hours in a mixture containing 50 ml of acetic acid and 50 ml of ethanol, and is then concentrated under reduced pressure. This residue is purified by chromatography on a column of silica gel, eluting with a methanol/dichloromethane mixture (5/95).

1.2 g of product are obtained in base form.
Yield=75%

The hydrochloride is prepared by dissolving 1.2 g (1.8 mmol) of base in 36 ml of a solution of isopropanol in 0.1N hydrochloric acid and evaporating under reduced pressure.

Melting point=74° C.

$[\alpha]_D^{20}$=+60° (c=0.2; methanol)

EXAMPLE 2 (COMPOUND NO. 15)

Ethyl [2R-[1(S), 2α, 4β]]-4-ethyl-1-[5-(5-methyl-1H-imidazol-4-yl)-2-[[[3'-methyl-2-[(1-oxopropyl)amino][1,1'-biphenyl]-3-yl]sulphonyl]amino]-1-oxopentyl]piperidine-2-carboxylate hydrochloride

2.1. N,N-diethylethanamine salt of 2-[bis(1-oxopropyl)amino]-3'-methyl[1,1'-biphenyl]-3-sulphonic acid 2.1 g (8 mmol) of 2-amino-3'-methyl[1,1'-biphenyl]-3-sulphonic acid are dissolved in 10 ml of dichloromethane, 1.34 ml (9.6 mmol) of triethylamine are added and the mixture is evaporated to dryness. The salt obtained is then dissolved in 15.5 ml of propionic anhydride, and the mixture is heated for 8 hours at 100° C. and evaporated to dryness. The residue is purified by chromatography on a column of silica gel, eluting with a dichloromethane/ethanol/triethylamine mixture (98/2/0.001).

3.6 g of product are obtained in the form of a viscous oil which is used without further purification in the following step.

Yield=95%

2.2. 2-[bis(1-oxopropyl)amino]-3'methyl[1,1'-biphenyl]-3-sulphonyl chloride To a solution of 3.6 g (7.6 mmol) of the N,N-diethylethanamine salt of 2-[bis(1-oxopropyl)amino]-3'-methyl[1,1'-biphenyl]-3-sulphonic acid in 8 ml of dichloromethane, at 0° C., are added 1.6 g (7.6 mmol) of phosphorus pentachloride and the mixture is allowed to return to room temperature. The mixture is then heated for 4 hours at the reflux temperature and is then allowed to return to room temperature. Ether is added, the mixture is filtered, the filtrate is concentrated and the residue is purified on a column of florisil™, eluting with an ether/pentane mixture (1/1). The product is recrystallized from an ether/pentane mixture.

1.7 g of product are obtained in the form of whitish crystals.

Yield=58%

Melting point=91° C.

2.3. ethyl [2R-[1(S), 2α, 4β]]-1-[2-[[[2-[bis(1-oxopropyl)amino]-3'methyl[1,1'-biphenyl]-3-yl]sulphonyl]amino]-5-[5-methyl-1-(triphenylmethyl)-1H-imidazol-4-yl]-1-oxopentyl]-4-ethylpiperidine-2-carboxylate 787 mg (2 mmol) of 2-[bis(1-oxopropyl)amino]-3'methyl [1,1'-biphenyl]-3-sulphonyl chloride are dissolved in 8 ml of dichloromethane and, at 0° C., 1.3 g (2 mmol) of ethyl [2R-[1(S), 2α, 4β]]-1-[2-amino-5-[5-methyl-1-(triphenylmethyl)-1H-imidazol-4-yl]-1-oxopentyl]-4-ethylpiperidine-2-carboxylate hydrochloride and 0.9 ml of triethylamine are added. The reaction mixture is allowed to warm to room temperature, it is evaporated and the residue is taken up in 100 ml of ethyl acetate. This solution is washed successively with 50 ml of 1N hydrochloric acid solution, 50 ml of saturated sodium hydrogen carbonate solution and 50 ml of saturated sodium chloride solution, dried over magnesium sulphate and then evaporated to dryness.

1.6 g of product are obtained, which product is used without further purification in the following step.

Yield=84%

2.4. ethyl [2R-[1(S), 2α, 4β]]-4-ethyl-1-[5-(5-methyl-1H-imidazol-4-yl)-2-[[[3'-methyl-2-[(1-oxopropyl)amino][1,1'-biphenyl]-3-yl]sulphonyl]amino]-1-oxopentyl]piperidine-2-carboxylate hydrochloride 1.6 g (1.7 mmol) of ethyl [2R-[1(S), 2α, 4β]]-1-[2-[[[2-[bis(1-oxopropyl)amino]-3'methyl[1,1'-biphenyl]-3-yl]sulphonyl]amino]-5-[5-methyl-1-(triphenylmethyl)-1H-imidazol-4-yl]-1-oxopentyl]-4-ethylpiperidine-2-carboxylate are dissolved in 85 ml of acetic acid and 17 ml of water, and the solution is heated to the reflux temperature for 6 hours. It is evaporated to dryness and the residue is taken up in 100 ml of ethyl acetate and washed successively with 20 ml of saturated sodium hydrogen carbonate solution and 10 ml of saturated sodium chloride solution, and then evaporated to dryness. The residue is purified by chromatography on a column of silica gel, eluting with a dichloromethane/ethanol mixture (95/5).

1 g of product is obtained in base form.

The hydrochloride is prepared in a solution of isopropanol in 0.1N hydrochloric acid and is again concentrated under reduced pressure. This residue is purified on an RP18 column, eluting with an acetonitrile/water mixture (1/1).

After freeze-drying, 893 mg of product are obtained.

Yield=67%

Melting point=140° C.

$[\alpha]_D^{20}$=+115° (c=0.2; methanol)

EXAMPLE 3 (COMPOUND NO. 3)

ethyl [2R-[1(S), 2α, 4β]]-4-ethyl-1-[5-(5-methyl-1H-imidazol-4-yl)-1-oxo-2-[[[2-[(1-oxopropyl)amino][1,1'-biphenyl]-3-yl]sulphonyl]amino]pentyl]piperidine-2-carboxylate hydrochloride

3.1. 2-[bis(1-oxopropyl)amino][1,1'-biphenyl]-3-sulphonyl chloride

The product is prepared according to the method described in Example 2, starting with 2-amino[1,1'-biphenyl]-3-sulphonic acid and propionic anhydride.

Melting point=113.8° C.

3.2. ethyl [2R-[1(S), 2α, 4β]]-1-[2-[[[2-[bis(1-oxopropyl)amino][1,1'-biphenyl]-3-yl]sulphonyl]amino]-5-[5-methyl-1-(triphenylmethyl)-1H-imidazol-4-yl]-1-oxopentyl]-4-ethylpiperidine-2-carboxylate 1.88 g (4.85 mmol) of 2-[bis(1-oxopropyl)amino][1,1'-biphenyl]-3-sulphonyl chloride are dissolved in 20 ml of dichloromethane and the mixture is placed at 0° C. 2.99 g (4.5 mmol) of ethyl [2R-[1(S), 2α, 4β]]-1-[2-amino-5-[5-methyl-1-(triphenylmethyl)-1H-imidazol-4-yl]-1-oxopentyl]-4-ethylpiperidine-2-carboxylate hydrochloride and, dropwise, 1.6 ml of triethylamine are then added. The mixture is left stirring at this temperature overnight. It is concentrated under reduced pressure and the residue is taken up in 100 ml of ethyl acetate and washed successively with 50 ml of 1N hydrochloric acid solution, with 50 ml of saturated sodium hydrogen carbonate solution and then with 50 ml of saturated sodium chloride solution. It is dried over magnesium sulphate and concentrated under reduced pressure. The residue is purified by chromatography on a column of silica gel, eluting with a dichloromethane/methanol mixture (98/2).

2.9 g of product are obtained.
Yield=62%

3.3. ethyl [2R-[1(S), 2α, 4β]]-4-ethyl-1-[5-(5-methyl-1H-imidazol-4-yl)-1-oxo-2-[[[2-[(1-oxopropyl)amino][1,1'-biphenyl]-3-yl]sulphonyl]amino]pentyl]piperidine-2-carboxylate hydrochloride To 2.9 g (3 mmol) of ethyl [2R-[1(S), 2α, 4β]]-1-[2-[[[2-[bis(1-oxopropyl)amino][1,1'-biphenyl]-3-yl]sulphonyl]amino]-5-[5-methyl-1-(triphenylmethyl)-1H-imidazol-4-yl]-1-oxopentyl]-4-ethylpiperidine-2-carboxylate are added 150 ml of acetic acid and 50 ml of water, and the mixture is heated at the reflux temperature for 6.5 hours. It is evaporated to dryness and the residue is purified by chromatography on a column of silica gel, eluting with a dichloromethane/methanol mixture (95/5).

1.7 g of product are obtained in base form.

The hydrochloride is prepared in 10 ml of a solution of isopropanol in 0.1N hydrochloric acid, and the mixture is again concentrated under reduced pressure. This residue is purified on an RP 18 column, eluting with an acetonitrile/water mixture (1/1).

1.3 g of product are obtained in the form of the hydrochloride.
Yield=63%
Melting point=104°–105° C.
$[\alpha]_D^{20}=+105°$ (c=0.2; methanol)

EXAMPLE 4 (COMPOUND NO. 29)

ethyl [2R-[1(S), 2α, 4β]]-4-ethyl-1-[5-(5-methyl-1H-imidazol-4-yl)-1-oxo-2-[[[2-[(1-oxopropyl)amino]-3-pyrid-2-ylphenyl]sulphonyl]amino]pentyl]piperidine-2-carboxylate hydrochloride

4.1. N,N-diethylethanamine salt of 2-[bis(1-oxopropyl)amino]-5-bromo-3-iodobenzenesulphonic acid A solution of 31.7 g (66 mmol) of the N,N-diethylethanamine salt of 2-amino-5-bromo-3-iodobenzenesulphonic acid in 114 ml (1.32 mol) of propionyl chloride is heated for 16 hours at the reflux temperature, then the reaction medium is concentrated under reduced pressure and the product is crystallized from 100 ml of ethyl acetate.

32.5 g of product are obtained in the form of white crystals.
Yield=84%
Melting point=124°–128° C.

4.2. 2-[bis(1-oxopropyl)amino]-5-bromo-3-iodobenzenesulphonyl chloride

To a solution of 32.5 g (55 mmol) of the N,N-diethylethanamine salt of 2-[bis(1-oxopropyl)amino]-5-bromo-3-iodobenzenesulphonic acid in dichloromethane are added portionwise, at 0° C. under nitrogen, 16.8 g (82.4 mmol) of phosphorus pentachloride. The mixture is allowed to warm to room temperature and is heated for 4 hours at the reflux temperature. 200 ml of ether are poured in, the mixture is filtered and the filtrate is concentrated. The residue is purified by chromatography on a column of florisil™ eluting with an ether/hexane mixture (2/8). The product is recrystallized from an ether/pentane mixture. 12 g of product are obtained in the form of white crystals.
Yield=43%
Melting point=127°–132° C.

4.3. ethyl [2R-[1(S), 2α, 4β]]-1-[2-[[[5-bromo-3-iodo-2-[(1-oxopropyl)amino]phenyl]sulphonyl]amino]-5-[5-methyl-1-(triphenylmethyl)-1H-imidazol-4-yl]-1-oxopentyl]-4-ethylpiperidine-2-carboxylate To a solution of 1.28 g (2 mmol) of ethyl [2R-[1(S), 2α, 4β]]-1-[2-amino-5-[5-methyl-1-(triphenylmethyl)-1H-imidazol-4-yl]-1-oxopentyl]-4-ethylpiperidine-2-carboxylate hydrochloride in dichloromethane are successively added, at 0° C. under nitrogen, 1.02 g (2 mmol) of 2-[bis(1-oxopropyl)amino]-5-bromo-3-iodobenzenesulphonyl chloride followed by dropwise addition of 0.69 μl (5 mmol) of triethylamine. The reaction medium is left stirring for 6 hours at 0° C. and is then taken up in 100 ml of ethyl acetate. Next, it is washed successively with twice 50 ml of 0.5N hydrochloric acid, 50 ml of saturated sodium hydrogen carbonate solution and 50 ml of saturated sodium chloride solution. Finally, the solution is dried over magnesium sulphate and concentrated under reduced pressure. 2.1 g of product are obtained in the form of a viscous oil, which is taken up in 100 ml of tetrahydrofuran and treated at 0° C. with ammonia gas. The reaction medium is left stirring for 2 hours at this temperature, and is concentrated under reduced pressure. The residue is purified by chromatography on a column of silica gel, eluting with a dichloromethane/methanol mixture (98/2). 1.4 g of product are obtained in the form of a viscous oil, which is used without further purification in the following step.
Yield=70%

4.4. ethyl [2R-[1(S), 2α, 4β]]-1-[2-[[[5-bromo-2-(1-oxopropyl)amino]-3-pyrid-2-ylphenyl]sulphonyl]amino]-5-[5-methyl-1-(triphenylmethyl)-1H-imidazol-4-yl]-1-oxopentyl]-4-ethylpiperidine-2-carboxylate A mixture containing 1.2 g (1.2 mmol) of ethyl [2R-[1(S), 2α, 4β]]-1-[2-[[[5-bromo-3-iodo-2-[(1-oxopropyl)amino]phenyl]sulphonyl]amino]-5-[5-methyl-1-(triphenylmethyl)-1H-imidazol-4-yl]-1-oxopentyl]-4-ethylpiperidine-2-carboxylate, 0.53 g (1.44 mmol) of 2-(tributylstannyl)pyridine, 14 mg (0.07 mmol) of copper iodide and 83 mg (0.07 mmol) of tetrakis(triphenylphosphine) palladium (0) in 2.4 ml of dimethylformamide is heated at 95° C. under argon for 4 hours. The reaction medium is then taken up in 100 ml of ethyl acetate, washed with twice 100 ml of 5% sodium hydrogen carbonate solution and then with 50 ml of saturated sodium chloride solution, dried over magnesium sulphate and concentrated under reduced pressure. The residue is purified by chromatography on a column of silica gel, eluting with a dichloromethane/methanol mixture (98/2).

0.72 g of product is obtained, which is used without further purification in the following step.

Yield=63%

Melting point=90°–94° C.

4.5. ethyl [2R-[1(S), 2α, 4β]]-1-[2-[[[5-bromo-2-[(1-oxopropyl)amino]-3-pyrid-2-ylphenyl]sulphonyl]amino]-5-[5-methyl-1H-imidazol-4-yl]-1-oxopentyl]-4-ethylpiperidine-2-carboxylate 0.71 g (0.75 mmol) of ethyl [2R-[1(S), 2α, 4β]]-1-[2-[[[5-bromo-2-[(1-oxopropyl)amino]-3-pyrid-2-ylphenyl]sulphonyl]amino]-5-[5-methyl-1-(triphenylmethyl)-1H-imidazol-4-yl]-1-oxopentyl]-4-ethylpiperidine-2-carboxylate in a mixture containing 35 ml of acetic acid and 10 ml of water is heated at 100° C. for 1 hour. The reaction medium is concentrated under reduced pressure and the residue is purified by chromatography on a column of silica gel, eluting with a methanol/dichloromethane mixture (5/95).

0.452 g of product is isolated in the form of a viscous oil, which is used without further purification in the following step.

Yield=83%

4.6. Ethyl [2R-[1(S), 2α, 4β]]-4-ethyl-1-[5-(5-methyl-1H-imidazol-4-yl)-1-oxo-2-[[[2-[1-oxopropyl)amino]-3-pyrid-2-ylphenyl]sulphonyl]amino]pentyl]piperidine-2-carboxylate hydrochloride A mixture of 0.45 g (0.61 mmol) of ethyl [2R-[1(S), 2α, 4β]]-1-[2-[[[5-bromo-2-[(1-oxopropyl)amino]-3-pyrid-2-ylphenyl]sulphonyl]amino]-5-[5-methyl-1H-imidazol-4-yl]-1-oxopentyl]-4-ethylpiperidine-2-carboxylate, 0.39 g (6 mmol) of ammonium formate and 50 mg of 10% palladium on charcoal in 8 ml of methanol and 0.2 ml of acetic acid is heated for 4 hours at the reflux temperature. The reaction medium is then concentrated under reduced pressure and the residue is purified by chromatography on a column of silica gel, eluting with a dichloromethane/methanol mixture (95/5).

0.36 g of product is obtained in the form of a viscous oil.

Yield=81%

The hydrochloride is prepared according to the method described in Example 3.

Melting point=78°–84° C.

$[\alpha]_D^{20}$=+91° (c=0.2; methanol)

EXAMPLE 5 (COMPOUND NO. 25)

Ethyl [2R-[1(S), 2α, 4β]]-4-ethyl-1-[5-(5-methyl-1H-imidazol-4-yl)-2-[[[3',5'-dimethyl-2-[(1-oxobutyl)amino][1,1'-biphenyl]-3-yl]sulphonyl]amino]-1-oxopentyl]piperidine-2-carboxylate hydrochloride

5.1. N,N-diethylethanamine salt of 2-[(3',5'-dimethyl)-2-(1-oxobutyl)amino][1,1'-biphenyl]-3-sulphonic acid 2 g (7.2 mmol) of 2-amino-3',5'-dimethyl[1,1'-biphenyl]-3-sulphonic acid in 8.3 ml (50 mmol) of butyric anhydride are heated for 2 hours at 80° C. The medium is allowed to warm to room temperature and is concentrated under reduced pressure. The residue is purified by chromatography on an RP 18 column, eluting with an acetonitrile/water mixture (2/8).

1.5 g of product are obtained in the form of a white solid. The triethylamine salt is prepared according to the method described in Example 2, and is used without further purification in the following step.

Yield=60%

5.2. N,N-diethylethanamine salt of 2-[(3',5'-dimethyl)-2-[(1-oxobutyl)(trifluoroacetyl)amino][1,1'-biphenyl]-3-sulphonic acid A mixture of 1.48 g (3.3 mmol) of the N,N-diethylethanamine salt of 2-[(3',5'-dimethyl)-2-(1-oxobutyl)amino][1,1'-biphenyl]-3-sulphonic acid and 4.7 ml (33 mmol) of trifluoroacetic anhydride is heated at the reflux temperature for 1 hour, and the reaction medium is then concentrated under reduced pressure.

1.8 g of product are obtained in the form of a viscous oil, which product is used without further purification in the following step.

Yield=100%

5.3. 2-[(3',5'-dimethyl)-2-[(1 -oxobutyl)(trifluoroacetyl)amino][1,1'-biphenyl]-3-sulphonyl chloride To a solution of 1.8 g (3.3 mmol) of the N,N-diethylethanamine salt of 2-[(3',5'-dimethyl)-2-[(1-oxobutyl)(trifluoroacetyl)amino][1,1-biphenyl]-3-sulphonic acid in 10 ml of dichloromethane are added, at room temperature under nitrogen, 1.37 g (6.6 mmol) of phosphorus pentachloride, the mixture is heated at the reflux temperature for 4 hours and the reaction medium is then allowed to cool to room temperature, 100 ml of ether are poured in and the mixture is filtered then concentrated under reduced pressure. The residue thus obtained is purified by chromatography on a florisil™ column, eluting with dichloromethane.

0.78 g of product is obtained in the form of a viscous oil, which is used without further purification in the following step.

Yield=51%

NMR (CDCl$_3$), 200 Mhz, δ, (ppm): 8.3 (dd, 1H, J=6.5 Hz, J=0.7 Hz); 7.85–7.7 (m, 2H); 7.15–7.00 (m, 1H), 6.8 (s, 2H); 2.5–2.3 (m, 7H); 1.75–1.5 (m, 3H); 0.9 (t, 3H, 6Hz)

5.4. ethyl [2R-[1(S), 2α, 4β]]-4-ethyl-1-[5-(5-methyl-1H-imidazol-4-yl)-2-[[[3',5'-dimethyl-2-[(1-oxobutyl)amino][1,1'-biphenyl]-3-yl]sulphonyl]amino]-1-oxopentyl]piperidine-2-carboxylate hydrochloride To a solution of 0.554 g (1.2 mmol) of 2-[(3',5'-dimethyl)-2-[(1-oxobutyl)(trifluoroacetyl)amino][1,1'-biphenyl]-3-sulphonyl chloride in 5 ml of dichloromethane is added, at 0° C. under nitrogen, 0.815 g (1.2 mmol) of ethyl [2R-[1(S), 2α, 4β]]-1-[2-amino-5-[5-methyl-1-(triphenylmethyl)-1H-imidazol-4-yl]-1-oxopentyl]-4-ethylpiperidine-2-carboxylate hydrochloride followed by dropwise addition of 0.56 ml (4 mmol) of triethylamine. The reaction medium is left stirring at this temperature for 6 hours and is then concentrated under reduced pressure. The residue is taken up in 100 ml of ethyl acetate and is then washed successively with 50 ml of aqueous 0.5N hydrochloric acid solution, then with 50 ml of aqueous 5% sodium hydrogen carbonate solution and then with 50 ml of saturated sodium chloride solution, and dried over magnesium sulphate. The organic phase is concentrated under reduced pressure.

1 g of product is obtained, which is used without further purification in the following step.

The residue is heated for 2 hours at the reflux temperature in a mixture containing 12 ml of acetic acid, 6 ml of tetrahydrofuran and 6 ml of water, and the reaction medium is then concentrated under reduced pressure. The residue is purified on a column of silica, eluting with a methanol/water mixture (5/95).

0.475 g of product is obtained in base form in the form of a viscous oil.

Yield=56%

The hydrochloride is prepared by dissolving 0.475 g of base in 14 ml of a solution of isopropanol in 0.1N hydrochloric acid.

Melting point=135° C.

$[\alpha]_D^{20}$=+118° (c=0.2; methanol)

EXAMPLE 6 (COMPOUND NO. 34)

ethyl [2R-[1(S), 2α, 4β]]-4-ethyl-1-[5-(5-methyl-1H-imidazol-4-yl)-1-oxo-2-[[[2-[(1-oxopropyl)amino]-3-thien-2-ylphenyl]sulphonyl]amino]pentyl]piperidine-2-carboxylate hydrochloride

6.1. N,N-diethylethanamine salt of 2-[bis(1-oxopropyl)amino]-3-thien-2-ylbenzenesulphonic acid 1.9 g (7.8 mmol) of 2-amino-3-thien-2-ylbenzenesulphonic acid are dissolved in 10 ml of dichloromethane, 1.3 ml (9.4 mmol) of triethylamine are added and the mixture is evaporated to dryness. The salt obtained is then dissolved in 15 ml of propionic anhydride, and the mixture is heated for 8 hours at 150° C. and evaporated to dryness. The residue is purified by chromatography on a column of silica gel, eluting with a dichloromethane/ethanol/triethylamine mixture (98/2/0.001).

2.76 g of product are obtained after recrystallization from ethyl acetate.

Yield=79%

6.2. 2-[bis(1-oxopropyl)amino]-3-thien-2-ylbenzenesulphonyl chloride

To a solution of 2.8 g (6.1 mmol) of the N,N-diethylethanamine salt of 2-[bis(1-oxopropyl)amino]-3-thien-2-ylbenzenesulphonic acid in 6 ml of dichloromethane are added, at 0° C., 1.3 g (6.1 mmol) of phosphorus pentachloride and the reaction mixture is allowed to warm to room temperature. The mixture is then heated for 5 hours at the reflux temperature and then allowed to cool to room temperature. Ether is added, the mixture is filtered and the residue is precipitated from an ether/pentane mixture (1/1). The mixture is filtered and the filtrate is concentrated under reduced pressure and purified by chromatography on a column of florisil™. 2.2 g of product are obtained, which product is crystallized from an ether/pentane mixture.

1.5 g of product are obtained in the form of white crystals.

Yield=55%

Melting point=113.6° C.

6.3. ethyl [2R-[1(S), 2α, 4β]]-1-2-[[[2-[bis(1-oxopropyl)amino]-3-thien-2-ylphenyl]sulphonyl]amino]-5-[5-methyl-1-(triphenylmethyl)-1H-imidazol-4-yl]-1-oxopentyl]-4-ethylpiperidine-2-carboxylate 0.9 g (2 mmol) of 2-[bis(1-oxopropyl)amino]-3-thien-2-ylbenzenesulphonyl chloride is dissolved in 8 ml of dichloromethane and the mixture is placed at 0° C. 1.3 g (2 mmol) of ethyl [2R-[[1(S), 2α, 4β]]-1-[2-amino-5-[5-methyl-1-(triphenylmethyl)-1H-imidazol-4-yl]-1-oxopentyl]-4-ethylpiperidine-2-carboxylate hydrochloride are then added, followed by dropwise addition of 0.9 ml of triethylamine. The mixture is left stirring at this temperature overnight. It is concentrated under reduced pressure and the residue is taken up in 100 ml of ethyl acetate and washed successively with 50 ml of 1N hydrochloric acid solution, with 50 ml of saturated sodium hydrogen carbonate solution and then with 50 ml of saturated sodium chloride solution. The solution is dried over magnesium sulphate and concentrated under reduced pressure. The residue is purified by chromatography on a column of silica gel, eluting with a dichloromethane/methanol mixture (98/2).

2 g of product are obtained, which product is used without further purification in the following step.

6.4. ethyl [2R-[1(S), 2α, 4β]]-4-ethyl-1-[5-(5-methyl-1H-imidazol-4-yl)-1-oxo-2-[[[2-[(1-oxopropyl)amino]-3-thien-2-ylphenyl]sulphonyl]amoino]pentyl]piperidine-2-carboxylate hydrochloride To 1.9 g (2 mmol) of ethyl [2R-[1(S), 2α, 4β]]-1-[2-[[[2-[bis(1-oxopropyl)amino]-3-thien-2-ylphenyl]sulphonyl]amino]-5-[5-methyl-1-(triphenylmethyl)-1H-imidazol-4-yl]-1-oxopentyl]-4-ethylpiperidine-2-carboxylate are added 100 ml of acetic acid and 20 ml of water, and the mixture is heated at the reflux temperature for 6 hours. It is evaporated to dryness and the residue is taken up in 100 ml of ethyl acetate and washed with 10 ml of saturated sodium hydrogen carbonate solution and then with 10 ml of saturated sodium chloride solution, dried over magnesium sulphate and evaporated to dryness. The residue is purified by chromatography on a column of silica gel, eluting with a dichloromethane/methanol gradient.

1.1 g of product are obtained in base form.

The hydrochloride is prepared in 10 ml of a solution of isopropanol in 0.1N hydrochloric acid, and is again concentrated under reduced pressure. This residue is purified on an RP 18 column, eluting with an acetonitrile/water mixture (1/1).

After freeze-drying, 0.939 g of product is obtained in the form of the hydrochloride.

Yield=67%

Melting point=151° C.

$[\alpha]_D^{20}$=+107° (c=0.2; methanol)

EXAMPLE 7 (COMPOUND NO. 42)

ethyl [2R-[1(S), 2α, 4β]]-1-[2-[[[2-(acetylamino)-3-cyclopentylphenyl]sulphonyl]amino]-5-(5-methyl-1H-imidazol-4-yl)-1-oxopentyl]-4-ethylpiperidine-2-carboxylate hydrochloride

7.1. N,N-diethylethanamine salt of 2-(diacetylamino)-3-cyclopentylbenzenesulphonic acid 3.42 g (10 mmol) of the N,N-diethylethanamine salt of 2-amino-3-cyclopentylbenzenesulphonic acid dissolved in 100 ml of acetyl chloride are heated at the reflux temperature for 48 hours, and the reaction medium is then concentrated under reduced pressure.

4.3 g of product are obtained in the form of an oil, which product is used without further purification in the following step.

Yield=100%

7.2. 2-(diacetylamino)-3-cyclopentylbenzenesulphonyl chloride

A solution of 1.55 g (3.6 mmol) of 2-(diacetylamino)-3-cyclopentylbenzenesulphonic acid and 1.12 g (5.4 mmol) of phosphorus pentachloride in 10 ml of dichloromethane is heated at the reflux temperature for 2.5 hours, and the reaction medium is then concentrated under reduced pressure. The residue thus obtained is purified by chromatography on a column of florisil™, eluting with dichloromethane.

0.62 g of product is obtained in the form of a viscous oil, which is used without further purification in the following step.

Yield=50%

7.3. ethyl [2R-[1(S), 2α, 4β]]-1-[2-[[[2-(diacetylamino)-3-cyclopentylphenyl]sulphonyl]amino]-5-[5-methyl-1-(triphenylmethyl)-1H-imidazol-4-yl]-1-oxopentyl]-4-ethylpiperidine-2-carboxylate To a mixture of 0.77 g (1.2 mmol) of ethyl [2R-[1(S), 2α, 4β]]-1-[2-amino-5-[5-methyl-1-(triphenylmethyl)-1H-imidazol-4-yl]-1-oxopentyl]-4-ethylpiperidine-2-carboxylate hydrochloride and 0.37 ml (2.64 mmol) of triethylamine in 5 ml of dichloromethane is added dropwise, at 0° C. under a nitrogen atmosphere, 0.35 g (1 mmol) of 2-(diacetylamino)-3-cyclopentylbenzenesulphonyl chloride dissolved in 1 ml of dichloromethane. The reaction medium is left stirring at this temperature for 6 hours and is then concentrated under reduced pressure. The residue is taken up in 50 ml of ethyl acetate and is then washed successively with 50 ml of aqueous 0.5N hydrochloric acid solution, with 50 ml of saturated sodium hydrogen carbonate solution and then with 50 ml of saturated sodium chloride solution, and dried over magnesium sulphate. The organic phase is concentrated under reduced pressure.

The residue is used without further purification in the following step.

7.4. ethyl [2R-[1(S), 2α, 4β]]-1-[2-[[[2-(acetylamino)-3-cyclopentylphenyl]sulphonyl]amino]-5-(5-methyl-1H-imidazol-4-yl)-1-oxopentyl]-4-ethylpiperidine-2-carboxylate hydrochloride ethyl [2R-[1(S), 2α, 4β]]-1-[2-[[[2-(diacetylamino)-3-cyclopentylphenyl]sulphonyl]amino]-5-[5-methyl-1-(triphenylmethyl)-1H-imidazol-4-yl]-1-oxopentyl]-4-ethylpiperidine-2-carboxylate is heated for 48 hours at the reflux temperature, in a mixture containing 8 ml of acetic acid, 4 ml of tetrahydrofuran and 4 ml of water, and the reaction medium is then concentrated under reduced pressure. The residue is taken up in 18 ml of a solution of isopropanol in 0.1N hydrochloric acid and is again concentrated under reduced pressure. This residue is purified on an RP 18 column, eluting with an acetonitrile/water mixture (6/4).

0.31 g of product is obtained in the form of the hydrochloride.

Yield=50%

Melting point=140° C.

$[\alpha]_D^{20} = +74.5°$ (c=0.25; methanol)

Key to the table: in the "salt" column: "chlor." represents a hydrochloride. The absence of an entry corresponds to the product in base form. In the "$[\alpha]_D^{20}$" column: c=0.2 except where otherwise mentioned; solvent=methanol.

TABLE

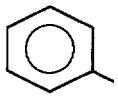

(I)

| No. | $R_1$ | $R_2$ | $R_3$ | $R_4$ | $R_5$ | A | Salt | m.p. (°C.) | $[\alpha]_D^{20}$ (°) |
|---|---|---|---|---|---|---|---|---|---|
| 1 | —CH₃ | —C₂H₅ | —CH₃ | —H | —C₂H₅ | 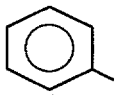 | chlor. | 136–141 | +128.8 (c = 0.25) |
| 2 | —CH₃ | H | —CH₃ | —H | —C₂H₅ | 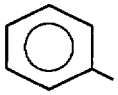 | chlor. | 165–170 | +92.4 (c = 0.25) |
| 3 | —CH₃ | —C₂H₅ | —C₂H₅ | —H | —C₂H₅ |  | chlor. | 104–105 | +105 |

TABLE-continued
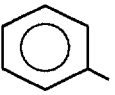# (I)
| No. | $R_1$ | $R_2$ | $R_3$ | $R_4$ | $R_5$ | A | Salt | m.p. (°C.) | $[\alpha]_D^{20}$ (°) |
|---|---|---|---|---|---|---|---|---|---|
| 4 | —CH₃ | —C₂H₅ | —C₃H₇ | —H | —C₂H₅ | 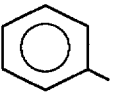 | chlor. | 95 | +109.5 |
| 5 | —H | —C₂H₅ | —CH₃ | —H | —CH₃ | 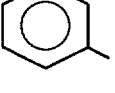 | chlor. | 125 | +103 |
| 6 | —H | —H | —CH₃ | —H | —CH₃ | 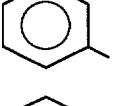 | chlor. | 168–175 | +68.4 (c = 0.25) |
| 7 | —H | —C₂H₅ | —C₂H₄OCH₃ | —Br | —C₂H₅ | 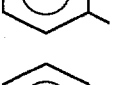 | chlor. | 120 | +52.5 |
| 8 | —H | —C₂H₅ | —C₂H₄OCH₃ | —H | —C₂H₅ | 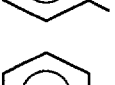 | chlor. | 74 | +60 |
| 9 | —H | —H | —C₂H₄OCH₃ | —H | —C₂H₅ | 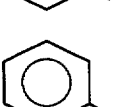 | chlor. | 132 | +59 |
| 10 | —H | —C₂H₅ | —C₃H₇ | —Br | —C₂H₅ | 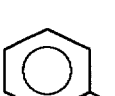 | chlor. | 121 | +83 |
| 11 | —H | —C₂H₅ | —C₃H₇ | —H | —C₂H₅ | 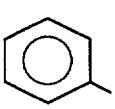 | chlor. | 125–127 | +124 |
| 12 | —H | —H | —C₃H₇ | —H | —C₂H₅ | 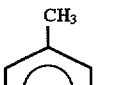 | chlor. | 141 | +116 |
| 13 | —H | —C₂H₅ | —CH₂O(C₂H₄O)₂CH₃ | —H | —C₂H₅ | 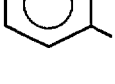 | chlor. | 74 | +77 |
| 14 | —CH₃ | —C₂H₅ | —CH₃ | —H | —C₂H₅ | CH₃-phenyl | chlor. | 134 | +113 |

TABLE-continued (I) [structure shown: R3OCHN and A on benzene ring; SO2NH linked to chiral center with C(=O)N-piperidine bearing CO-OR2 and R5; chain with R1 and imidazole; R4 on ring]

| No. | R₁ | R₂ | R₃ | R₄ | R₅ | A | Salt | m.p. (°C.) | $[\alpha]_D^{20}$ (°) |
|---|---|---|---|---|---|---|---|---|---|
| 15 | —CH₃ | —C₂H₅ | —C₂H₅ | —H | —C₂H₅ | 3-CH₃-phenyl | chlor. | 140 | +115 |
| 16 | —CH₃ | —C₂H₅ | —C₃H₇ | —H | —C₂H₅ | 3-CH₃-phenyl | chlor. | 120 | +112.5 |
| 17 | —CH₃ | —C₂H₅ | —C₂H₅ | —H | —C₂H₅ | 4-CH₃-phenyl | chlor. | 128 | +94 |
| 18 | —CH₃ | —C₂H₅ | —C₂H₅ | —H | —C₂H₅ | 2-CH₃-phenyl | chlor. | 130 | +110 |
| 19 | —CH₃ | —C₂H₅ | —CH₃ | —H | —C₂H₅ | 3-C₂H₅-phenyl | chlor. | 136 | +110 |
| 20 | —CH₃ | —C₂H₅ | —C₂H₅ | —H | —C₂H₅ | 3-C₂H₅-phenyl | chlor. | 108 | +103 |
| 21 | —CH₃ | —C₂H₅ | —C₂H₅ | —H | —C₂H₅ | 3-Cl-phenyl | chlor. | 154 | +103 |
| 22 | —CH₃ | —C₂H₅ | —C₂H₅ | —H | —C₂H₅ | 3-F-phenyl | chlor. | 126 | +54 |
| 23 | —CH₃ | —C₂H₅ | —C₃H₇ | —H | —C₂H₅ | 3-OCH₃-phenyl | chlor. | 65 | +104.5 |

TABLE-continued (I)

| No. | R₁ | R₂ | R₃ | R₄ | R₅ | A | Salt | m.p. (°C.) | [α]$_D^{20}$ (°) |
|---|---|---|---|---|---|---|---|---|---|
| 24 | —CH₃ | —C₂H₅ | —C₂H₅ | —H | —C₂H₅ | 2-methoxyphenyl | chlor. | 128 | +54 |
| 25 | —CH₃ | —C₂H₅ | —C₃H₇ | —H | —C₂H₅ | 3,5-dimethylphenyl | chlor. | 135 | +118 |
| 26 | —CH₃ | —C₂H₅ | —C₂H₅ | —H | —C₂H₅ | 3,5-dichlorophenyl | chlor. | 130 | +125 |
| 27 | —H | —C₂H₅ | —CH₃ | —H | —C₂H₅ | 2-pyridyl | chlor. | 131 | +42.5 |
| 28 | —H | —H | —CH₃ | —H | —C₂H₅ | 2-pyridyl | chlor. | 172 | +57 |
| 29 | —CH₃ | —C₂H₅ | —C₂H₅ | —H | —C₂H₅ | 2-pyridyl | chlor. | 78–84 | 91 |
| 30 | —CH₃ | —C₂H₅ | —CH₃ | —H | —C₂H₅ | 2-thienyl | chlor. | 178.2 | +97.6 (c = 0.25) |
| 31 | —CH₃ | —H | —CH₃ | —H | —C₂H₅ | 2-thienyl | chlor. | 150–155 | +111 (c = 0.55) |
| 32 | —H | —C₂H₅ | —CH₃ | —H | —C₂H₅ | 2-thienyl | chlor. | 90 | +73 |
| 33 | —H | —H | —CH₃ | —H | —C₂H₅ | 2-thienyl | chlor. | 150 | +82.5 |
| 34 | —CH₃ | —C₂H₅ | —C₂H₅ | —H | —C₂H₅ | 2-thienyl | chlor. | 151 | +107 |

TABLE-continued
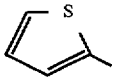
(I)
| No. | R₁ | R₂ | R₃ | R₄ | R₅ | A | Salt | m.p. (°C.) | [α]$_D^{20}$ (°) |
|---|---|---|---|---|---|---|---|---|---|
| 35 | —CH₃ | —C₂H₅ | —C₃H₇ | —H | —C₂H₅ | 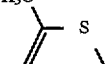 | chlor. | 124 | +101 |
| 36 | —CH₃ | —C₂H₅ | —C₃H₇ | —H | —C₂H₅ | 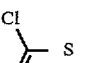 | chlor. | 110 | +52.6 |
| 37 | —CH₃ | —C₂H₅ | —C₂H₅ | —H | —C₂H₅ | 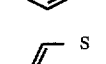 | chlor. | 132 | +63 |
| 38 | —CH₃ | —C₂H₅ | —C₃H₇ | —H | —CH₃ | 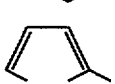 | chlor. | 130–132 | +132 |
| 39 | —CH₃ | —C₂H₅ | —C₂H₅ | —H | —C₂H₅ |  | chlor. | 128–134 | +57 |
| 40 | —H | —C₂H₅ | —CH₃ | —H | —C₂H₅ |  | chlor. | 124 | +78 |
| 41 | —H | —H | —CH₃ | —H | —C₂H₅ | 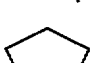 | chlor. | 149 | +102 |
| 42 | —CH₃ | —C₂H₅ | —CH₃ | —H | —C₂H₅ | 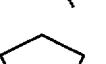 | chlor. | 140 | +74.5 |
| 43 | —CH₃ | —H | —CH₃ | —H | —C₂H₅ | 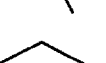 | chlor. | 160 | +81.5 |
| 44 | —CH₃ | —C₂H₅ | —C₂H₅ | —H | —C₂H₅ | 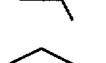 | chlor. | 118 | +93 |
| 45 | —H | —C₂H₅ | —C₃H₇ | —H | —C₂H₅ | 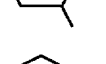 | chlor. | 125 | +73.5 |
| 46 | —CH₃ | —C₂H₅ | —C₃H₇ | —H | —CH₃ |  | chlor. | 132 | +104 |

TABLE-continued

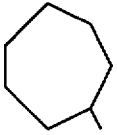

| No. | $R_1$ | $R_2$ | $R_3$ | $R_4$ | $R_5$ | A | Salt | m.p. (°C.) | $[\alpha]_D^{20}$ (°) |
|---|---|---|---|---|---|---|---|---|---|
| 47 | —H | —$C_2H_5$ | —$C_3H_7$ | —H | —$C_2H_5$ | cycloheptyl | chlor. | 120 | +77 |

The compounds of the invention formed the subject of pharmacological studies which demonstrated their antithrombotic properties and their advantage as substances having therapeutic activity.

1. Determination of the Inhibition Constants (Ki) With Respect to Thrombin

25 µl of a solution of test compound (7 concentrations are studied), 50 µl of a solution of chromogenic substrate (2 concentrations are studied; S2238 Chromogenix™) dissolved in Tris buffer at pH 7.5 (50 mM Tris, 100 mM NaCl and 0.1% BSA) and finally 25 µl of a 300 U/ml thrombin solution are placed in each well of a 96-well microplate. The release of 4-nitroaniline is monitored at 405 nm using a plate reader.

The $K_i$ is determined according to the Dixon method.

The compounds of the invention are thrombin inhibitors and their $K_i$ is between 0.001 and 100 µM.

2. Ex Vivo Coagulation of Rat Plasma by Human Thrombin

Male CD rats weighing 150 to 200 g are treated with the test compound or with the vehicle, via the i.v., oral or subcutaneous route. The animals are then anaesthetized with Nembutal™ (60 mg/kg; 0.1 ml/kg), the blood is withdrawn over 3.8% trisodium citrate (1 vol/9 vol of blood) from the retroorbital sinus and the plasma is prepared by centrifugation at 3600 g for 15 minutes at room temperature. 200 µl of plasma are then incubated at 37° C. with 200 βl of a solution of human thrombin, the final human thrombin concentration being 0.75 NIH units/ml, and the coagulation time is noted. The anticoagulant effect is expressed as the dose which increases the coagulation time by 100%. The compounds of the invention inhibit the coagulation of rat plasma at doses of from 0.01 to 5 mg/kg i.v. They are also active via the oral and subcutaneous routes.

3. Aggregation of Rabbit Platelets Induced by Human Thrombin

The blood is withdrawn by cardiac puncture onto 3.8% trisodium citrate (1 vol/9 vol of blood). It is centrifuged at 250 g for 10 minutes. The platelet-rich plasma ($P_3P$) thus obtained is withdrawn and the platelets are counted.

2 ng/ml of prostacyclin dissolved in ice-cold Tris buffer at pH 9.0 are added to the $P_3P$. The mixture is centrifuged at 110 g for 10 minutes and is decanted. Further prostacyclin, dissolved in 50 mM sodium hydroxide at pH 12, is added, so as to have a final concentration of 200 ng/ml. The $P_3P$ is again centrifuged, at 800 g for 10 minutes. The platelet-poor plasma is removed and the pellet is suspended in a volume of tyrode containing 200 ng/ml of prostacyclin, this volume being equal to the initial volume of $P_3P$. This suspension is centrifuged at 800 g for 10 minutes. Suspension of the pellet and centrifugation are repeated under the same conditions. The final pellet is suspended in a prostacyclin-free tyrode solution and is left to stand for 2 hours in order to allow complete removal of the prostacyclin. The aggregation of these platelets is induced with human thrombin to the final concentration of 0.3 NIH units/ml. The variations in optical density are recorded using a 4-channel aggregometer. The test compound or its vehicle is added to the platelet suspension (maximum volume of 3 µl added), 2 minutes before the addition of thrombin. The concentration which inhibits the aggregation by 50% ($IC_{50}$) is determined.

The compounds of the invention may be useful in all the clinical indications associated with thrombosis or in those in which thrombotic complications may be involved.

The present invention also provides a pharmaceutical composition comprising a compound of formula (I) and a pharmaceutically acceptable excipient. This composition may be provided in all forms suitable for oral, parenteral or intravenous administration, such as a tablet, dragee, gelatin capsule, wafer capsule, injectable or drinkable solution or suspension. All of these forms are dosed to allow an administration of 1 to 1000 mg per day and per patient, in one or more doses.

The present invention also provides a compound of formula (I) for use in a method of treatment of the human or animal body.

The present invention further provides the use of a compound of formula (I) in the manufacture of a medicament for the treatment of thrombosis or thrombotic complications.

There is also disclosed a method of treating or preventing thrombosis or thrombotic complications in a subject which comprises administering to that subject an effective amount of a compound of formula (I).

We claim:

1. A compound of formula (XI)

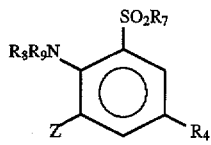

(XI)

in which (1) $R_8$ represents a hydrogen atom or a trifluoroacetyl group, $R_9$ represents a group —$COR_3$ where $R_3$ is a straight or branched ($C_1$–$C_7$)alkyl group, a group —$(CH_2)_nOCH_3$ (where n is 1, 2 or 3) or a group —$CH_2O(C_2H_4O)_mCH_3$ (where m is 1, 2 or 3) and $R_7$ represents a hydroxyl group, or (2) $R_8$ represents a trifluoroacetyl group, $R_9$ represents a group —$COR_3$ and $R_7$ represents a chlorine atom, or (3) $R_8$ and $R_9$ each represents a group —$COR'_3$ where $R'_3$ is a straight or branched ($C_1$–$C_7$)alkyl group and $R_7$ represents a chlorine atom or a hydroxyl group, Z represents an iodine atom, a phenyl or 5- to 6-membered heterocyclic ring having one or more heteroatoms which may be the same or different selected from the group consisting of nitrogen, oxygen and sulfur, the phenyl or the heterocyclic ring being optionally substituted with one or more substituents independently chosen from halogen atoms and straight or branched ($C_1$–$C_4$)alkyl, straight or branched ($C_1$–$C_4$)alkoxy and trifluoromethyl groups, or a cyclo ($C_5$–$C_8$)alkyl group, and $R_4$ is a hydrogen atom or a halogen atom.

* * * * *